(12) United States Patent  (10) Patent No.: US 7,558,362 B2
Shechter et al.  (45) Date of Patent: Jul. 7, 2009

(54) STREAK ARTIFACT REDUCTION IN CARDIAC CONE BEAM CT RECONSTRUCTION

(75) Inventors: Gilad Shechter, Haifa (IL); Galit Naveh, Haifa (IL)

(73) Assignee: Koninklijke Philips Electronics N.V., Eindhoven (NL)

( * ) Notice: Subject to any disclaimer, the term of this patent is extended or adjusted under 35 U.S.C. 154(b) by 433 days.

(21) Appl. No.: 11/571,660

(22) PCT Filed: Jun. 23, 2005

(86) PCT No.: PCT/IB2005/052079

§ 371 (c)(1),
(2), (4) Date: Jan. 5, 2007

(87) PCT Pub. No.: WO2006/006090

PCT Pub. Date: Jan. 19, 2006

(65) Prior Publication Data

US 2007/0195925 A1   Aug. 23, 2007

Related U.S. Application Data

(60) Provisional application No. 60/585,968, filed on Jul. 7, 2004.

(51) Int. Cl.
*A61B 6/03* (2006.01)
(52) U.S. Cl. .............................. 378/4; 378/19
(58) Field of Classification Search ............ 378/4, 378/19
See application file for complete search history.

(56) References Cited

U.S. PATENT DOCUMENTS 4,580,219 A   4/1986   Pelc et al.

(Continued)

FOREIGN PATENT DOCUMENTS

EP   0 751 484 A2   1/1997

(Continued)

OTHER PUBLICATIONS

La Riviere, Reduction of noise-induced streak artifacts in x-ray computed tomography through penalized-likelihood sinogram smoothing, Oct. 25, 2003, IEEE, Nuclear Science Symposium Conference Record, pp. 3239-3243.*

(Continued)

*Primary Examiner*—Edward J Glick
*Assistant Examiner*—John M Corbett

(57) ABSTRACT

In a diagnostic imaging system (10) two-dimensional projection data is collected in a data memory (30). The data is sorted into the data sets collected during selected cardiac phases. A re-binning processor (38) re-bins the projection data into a parallel ray format. An adaptive filter (70) filters the parallel ray format data with each of a plurality of different filter channels based on a calculated photonic noise of each reading and assuming an arbitrary noise reduction factor, different for each filter channel. A convolver (78) convolves the data filtered with each of the filter channels. A noise reduction factor processor (84) determines the actual noise reduction factor occurring due to the weighted averaging of readings contributing to each voxel v at an angle $\theta \in [0, 7\pi)$. A weighting processor (90) weights the convolved data from each of the filter channels based on the channels' noise reduction factors and the actual noise reduction factor. A backprojector (98) backprojects the combined weighted sum of projections to build an image representation that can be displayed in a human readable format.

22 Claims, 2 Drawing Sheets

U.S. PATENT DOCUMENTS

Figure 1:
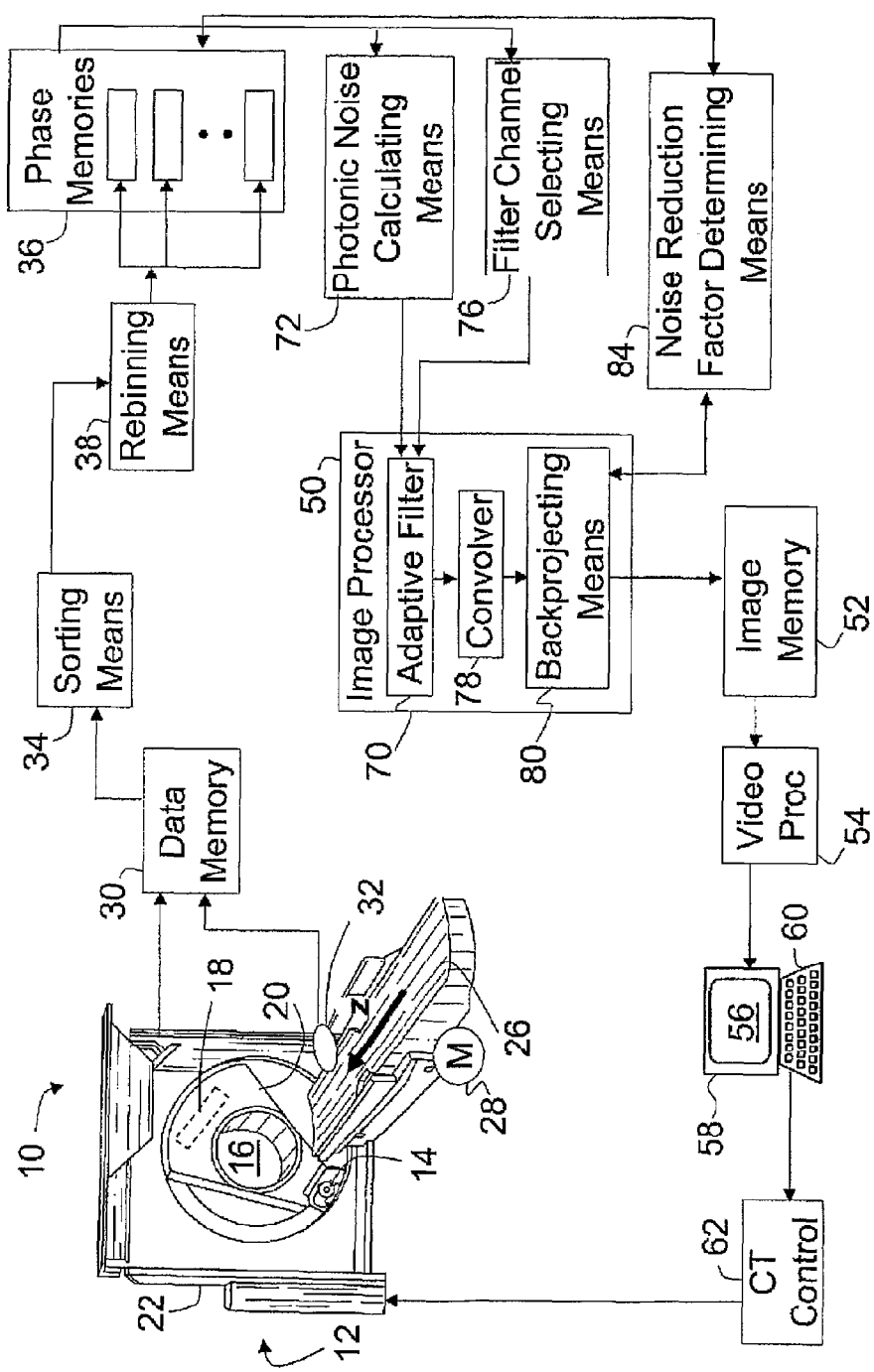

| | | | |
|---|---|---|---|
| 5,680,426 | A | 10/1997 | Ching-Ming |
| 5,987,091 | A | 11/1999 | Miyazaki et al. |
| 6,104,775 | A | 8/2000 | Tuy |
| 6,542,571 | B2 | 4/2003 | Zonneveld |
| 2002/0131650 | A1 | 9/2002 | Rodet et al. |
| 2002/0150200 | A1* | 10/2002 | Zonneveld ............... 378/4 |
| 2003/0007592 | A1* | 1/2003 | Timmer ............... 378/4 |
| 2003/0007593 | A1 | 1/2003 | Heuscher et al. |
| 2003/0071220 | A1* | 4/2003 | Bruder et al. ............... 250/369 |
| 2003/0076988 | A1 | 4/2003 | Liang et al. |
| 2004/0076265 | A1 | 4/2004 | Heuscher et al. |

FOREIGN PATENT DOCUMENTS

EP  0 997 849 A2  5/2000

OTHER PUBLICATIONS

Shechter et al., High-resolution images of cone beam collimated CT scans, Oct. 25, 2003, IEEE, Nuclear Science Symposium Conference Record, pp. 2973-2977.*

Shechter et al., Cardiac image reconstruction on a 16-slice CT scanner using a retrospectively ECG-gated, multi-cycle 3D back-projection algorithm, Feb. 17, 2003, SPIE, vol. 5032, pp. 1820-1828.*

Manzke et al., Extended Cardiac Reconstruction (ECR): A helical cardiac cone beam reconstruction method, Jun. 30, 2003, Proceedings of the VII International Conference on Fully 3D Reconstruction in Radiology and Nuclear Medicine, Mo-PM2-4, pp. 59-62.*

Kachelriess et al., Extended Parallel Backprojection (EPBP) for Arbitrary Cone Angle and Arbitrary Pitch 3D and Phase-Correlated 4D CT Reconstruction, Jul. 1, 2003, Proceedings of the VII International Conference on Fully 3D Reconstruction in Radiology and Nuclear Medicine, Tu-AM2-3, pp. 107-111.*

Grass et al., Helical cardiac cone beam reconstruction using retrospective ECG gating, Sep. 3, 2003, Physics in Medicine and Biology, vol. 48, pp. 3069-3084.*

Grass, M., et al.; Helical cardiac cone beam reconstruction using retrospective ECG gating; 2003; Phys. Med. Biol.; vol. 48; pp. 3069-3084.

Hsieh, J.; Adaptive streak artifact reduction in computed tomography resulting from excessive x-ray photon noise; 1998; Med. Phys.; 25(11)2139-2147.

Kachelriess, M., et al.; Generalized multi-dimensional adaptive filtering for conventional and spiral single-slice, multi-slice, and cone-beam CT; 2001; Med. Phys.; 28(4)475-490.

Li, T., et al.; A strategy for reduction of streak artifacts in low-dose CT; 2003; IEEE Conference on Medical Imaging.

Shecter, G., et al.; Cardiac image reconstruction on a 16-slice CT scanner using a retrospectively ECG-gated, multi-cycle 3D back-projection algorithm; 2003; Proc. of SPIE; vol. 5032; pp. 1820-1830.

Wang, G., et al.; A knowledge-based cone-beam x-ray CT algorithm for dynamic volumetric cardiac imaging; 2002; Med. Phys.; 29(8)1807-.

* cited by examiner

STREAK ARTIFACT REDUCTION IN CARDIAC CONE BEAM CT RECONSTRUCTION

CROSS REFERENCE TO RELATED APPLICATIONS

This application claims the benefit of U.S. provisional application serial no. 60/585,968 filed Jul. 7, 2004, which is incorporated herein by reference.

The present application relates to the diagnostic imaging arts. It finds particular application in cardiac computed tomography imaging of a subject, and will be described with particular reference thereto. However, it may also find application in other types of computed tomography imaging, single photon emission computed tomography (SPECT), positron emission tomography (PET), three-dimensional x-ray imaging, and the like.

In general, a computed-tomography system comprises an x-ray source and an x-ray detector which rotates around an object to be examined. From several orientations the object is irradiated with an x-ray beam from the x-ray source. At these respective orientations the x-ray detector receives x-radiation that has passed through the object and forms an attenuation profile for the orientation at issue. The attenuation profiles represent the attenuation of incident x-rays in the object due to scattering of x-rays and absorption of x-rays along the path of the x-rays through the object at the orientation at issue.

The quality of the CT image is often degraded by streaking artifacts resulting from excessive x-ray quantum noise. In the process of filtered backprojected reconstruction, all voxels are reconstructed from the rays available in the illumination window. Within the framework of approximate cone beam reconstruction algorithms, each sample in the projection space is mapped into a straight line in the image domain. The positive and negative contributions among neighboring lines are combined and no straight lines appear in the final image. When the contributions include noise, the reconstruction process is no longer able to properly combine the positive and negative contributions and a line or line segments, e.g. streaks, results. The streaks dramatically deteriorate image quality and can obliterate the structure of the region.

Cardiac cone beam images are reconstructed using phase selective algorithms. Typically, particular phases of the heart are chosen for cardiac image generation. Only data acquired close in time to the selected phases, i.e., the points in time corresponding to the same cardiac phase but in different heart cycles, are used in the reconstruction process. Depending on the scan parameters, the patient's heart rate and its variability, the cardiac gating window width and position, a variable number of cycles is used for reconstruction of each of the voxels. The time periods that fall within the cardiac gating window and the illumination window of each voxel determine the amount of redundant data available for each voxel in the reconstruction volume. During these time periods, the acquired data may have a non-uniform angular distribution. E.g., from 0 to 180 degrees there might be an angle where only one data point contributes to the reconstruction of a voxel, while for another angle, there will be contributions from three data points. Such non-uniform distribution leads to non-uniform noise and thus to a pattern noise streaks.

Several solutions for suppressing streak artifacts resulting from excessive photon noise have been suggested. One solution is to apply the adaptive filter to some points in the measured attenuation profiles. These filters are adaptive only to the differences in the noise contribution due to the anatomy of the patient and to variations in dose. The filter is modified to compensate for the higher x-ray photon noise in the high absorption angles. Neither the inhomogeneous distribution of the data which is used in the phase selective algorithm, nor the process of reconstruction is taken into consideration.

There is a need for a technique that suppresses streak artifacts in cardiac cone beam imaging that takes into consideration the noise of the readings, and the phase selective nature of the reconstruction algorithm. The present invention contemplates a method and apparatus that overcomes the aforementioned limitations and others.

According to one aspect of the present application, a diagnostic imaging system is disclosed. A means re-bins projection data into a parallel ray format. A means filters the parallel ray format data with each of a plurality of different filter channels, each channel with a different noise reduction factor. A means convolves the data filtered with each of the filter channels. A means performs a weighted averaging of readings which contribute to each voxel at an angle $\theta \in [0, \pi)$. A means determines actual noise reduction factors based on the weighted averaging. A means weights the convolved data for each of the filter channels based on the channels' noise reduction factors, and the determined actual noise reduction factors.

According to another aspect of the present application, a method for correcting streak artifacts in a cone beam CT imaging system is disclosed. Projection data is re-binned into a parallel ray format. The parallel ray format data is filtered with each of a plurality of different filter channels, each with a different noise reduction factor. The data filtered with each of the filter channels is convolved. Readings which contribute to each voxel at an angle $\theta \in [0, \pi)$ are weighted averaged. Actual noise reduction factors are determined based on the weighted averaging. The convolved data for each of the filter channels is weighted based on the channels' noise reduction factors, and the determined actual noise reduction factors.

One advantage of the present application resides in reducing streak artifacts.

Another advantage resides in simplicity of the technique which avoids voxel by voxel noise correction.

Another advantage resides in improved images from cardiac and other gated imaging techniques.

Numerous additional advantages and benefits will become apparent to those of ordinary skill in the art upon reading the following detailed description of the preferred embodiments.

The invention may take form in various components and arrangements of components, and in various process operations and arrangements of process operations. The drawings are only for the purpose of illustrating preferred embodiments and are not to be construed as limiting the invention.

Figure 2:
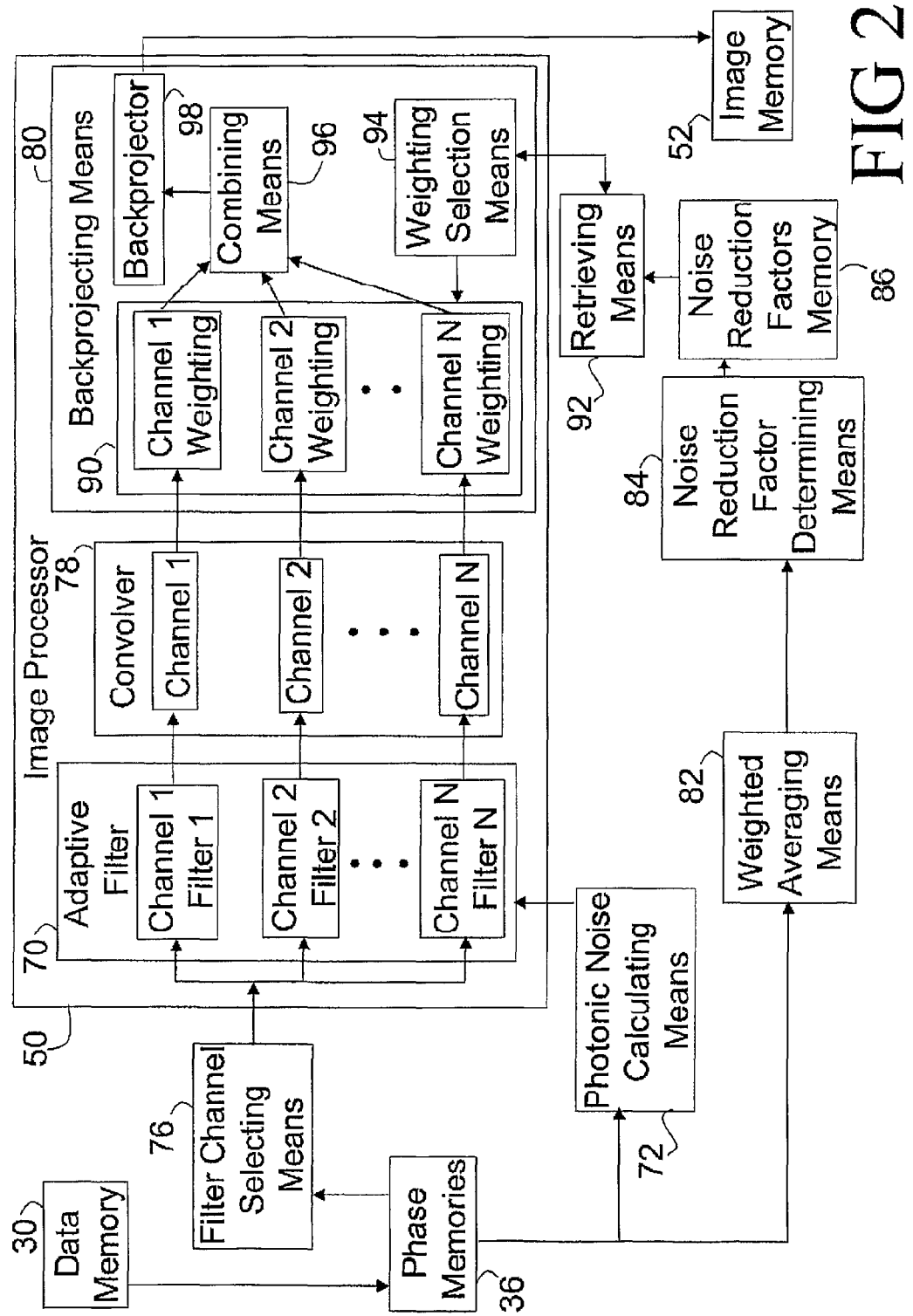

FIG. 1 diagrammatically shows a computed tomography imaging system including an adaptive filtering process according to the present application; and FIG. 2 diagrammatically shows a portion of a reconstruction process in which adaptive filtering is performed in the independent filter channels.

With reference to FIG. 1, an imaging system 10 includes a computed tomography scanner 12 having a radiation source 14 that produces a radiation beam, preferably a cone or wedge beam, directed into an examination region 16. The radiation beam interacts with and is partially absorbed as it traverses a region of interest of an imaging subject disposed in the examination region 16, producing spatially varying absorption of the radiation as it passes through the examination region. A radiation detector 18, preferably a two-dimensional detector, detects the absorption-attenuated radiation after it passes through the examination region 16. The path between the source 14 and each of radiation detection elements of the detector 18 is denoted as a ray.

Preferably, the radiation source 14 produces a cone-beam of x-rays. The radiation source 14 and the detector 18 are preferably mounted in oppositely facing fashion on a rotating gantry 20 so that the detector 18 continuously receives x-rays from the radiation source 14. As the source 14 and the detector 18 rotate continuously about the examination region 16 on the rotating gantry 20, views are acquired over a plurality of rotations. Each view or two-dimensional array of data represents a cone of rays having a vertex at the source 14 collected by a concurrent sampling of the detection elements of the detector 18. Typically, a subject support 26 is linearly movable in an axial or z-direction by a motor means 28.

Optionally, cone beam computed tomography projection data are acquired over several rotations either (i) with the subject support 26 being stationary during each axial scan and stepped linearly between axial scans or (ii) with the subject support moving continuously to define a helical trajectory. The outputs of the detection elements of the radiation detector 18 are converted to electric acquired integrated attenuation projection values $\mu d_o$ that are stored in a data memory 30. Each projection datum $\mu d_o$ corresponds to a line integral of attenuation along a line from the radiation source 14 to a corresponding one of the detection elements of the detector 18.

For typical cone-beam geometries, the line integral index typically corresponds to a detector element used to measure the reading. It is contemplated, however, that the line integral index may lack a direct correspondence with detector element number. Such a lack of direct correspondence can result, for example, from interpolation between re-binned projections.

A cardiac monitor 32 monitors the patient's cardiac cycle. A sorting means 34 sorts the attenuation data into data sets collected during each of the selected cardiac phases. The data sets are stored in a phase memories 36. Preferably, a re-binning processor 38 re-bins the data from cone to parallel beam geometry into a set of parallel views. Each view contains equidistant π-lines, where a π-line is defined as a line integral that is contained in the axial plane, i.e., perpendicular to the rotation axis, intersecting the scan FOV and is characterized by the canonic coordinates $\theta_\pi$ (angle of propagation $\epsilon[0, \pi)$) and 1 (distance from iso-center). Particularly for cardiac phases defined by a short temporal window, the data for one cardiac phase corresponds to data collected over short arc segments in each of a plurality of rotations, which arc segments of data individually are too small to be a full data set. When the data for each selected cardiac phase over a plurality of revolutions is concatenated, the number of rays corresponding to each π-line varies. Some π-lines may have three or four redundant attenuation data values which, after weighted averaging, would have a lower noise level because of redundancy noise reduction. Other π-lines may have only one data value which would retain its original noise level because no redundancy noise reduction would occur due to the weighed averaging. Since the noise reduction varies from one voxel to another, a voxel-dependent filtering is required leading to computational complexity. As will be discussed in a greater detail below, such complexity is avoided by applying an N-channel filtering that is not voxel dependent and postponing the influence of the voxel-dependent noise reduction to the backprojection step where the contributions of all channels are weighted on a voxel basis.

An image processor 50 processes the view data from the data for each selected cardiac phase into a corresponding three-dimensional image which is stored in an image memory 52. The detailed mathematical analysis of a preferred reconstruction is provided in U.S. Pat. No. 6,104,775 issued to Tuy. The attenuation data is adjusted during reconstruction to adjust for differences in redundancy and other noise differences. A video processor 54 processes some or all of the contents of the image memory 52 to create a human-viewable image representation such as a three-dimensional rendering, a selected image slice, a maximum intensity projection, a CINE animation, or the like. The human-viewable image representation is displayed on a display 56 of a user interface 58, which is preferably a personal computer, a workstation, a laptop computer, or the like. Optionally, selected contents of the image memory 52 are printed on paper, stored in a non-volatile electronic or magnetic storage medium, transmitted over a local area network or the Internet, or otherwise processed. Preferably, a radiologist or other operator controls the computed tomography imaging scanner 12 via an input means 60 to program a scan controller 62 to set up an imaging session, modify an imaging session, execute an imaging session, monitor an imaging session, or otherwise operate the scanner 12.

With continuing reference to FIG. 1 and further reference to FIG. 2, an adaptive filter 70 filters the data values of each selected cardiac phase in N independent filter channels which differ from each other by the type and degree of adaptive filter corrections. Each channel filters the data as a function of the data noise in a similar way, yet, by assuming this noise is reduced in a different degree, e.g. due to the weighted averaging over redundant readings. More specifically, a photonic noise calculating routine or means 72 calculates the photonic noise along the rays. The photonic noise is typically affected by several factors such as the attenuation line integral along the path (i.e. the anatomy of the patient), the tube current, and the like. Optionally, a priori about the patient's anatomy is incorporated to help to adjust the filtering functions since it is known that for certain paths it is more difficult for the x-ray photons to pass through and reach the detector.

At a particular angle $\theta \epsilon [0, \pi)$, a variable number of data points from different projections contributing to the angle $\theta$ might be obtained. A hybrid reading for a voxel v is the weighted sum of the readings of different projections that intersect the voxel v and are folded into the angle $\theta$. As a simplified example, for the voxel v at the angle $\theta$ there might be two projections each having a single point contributing to the voxel v. To make the calculations simpler, the assumption is made that the line integrals of the redundant data points are approximately the same. Further, the assumption is made that the number of photons corresponding to the redundant data points that reach the detectors are approximately the same. E.g., the noise approximation is made by assuming that the redundant data points have the same amount of inherent noise. A filter channel selecting means 76 selects an adaptive filter channel n$\epsilon[1, 2, \ldots, N]$ which has a noise reduction factor $NR^{n \epsilon [1, \ldots, N]} \epsilon [0, 1)$ corresponding to the redundancy of the voxel v at the angle $\theta$. In the example discussed above, where the two points contribute for the voxel v at the angle $\theta$ with the same cardiac weighting, the noise reduction is taken by a factor of $\sqrt{2}$, e.g. the filter channel selecting means 76 selects the adaptive filter channel n having a noise reduction factor $NR^{n \epsilon [1, \ldots, N]}$ of $$\frac{1}{\sqrt{2}}.$$

The noise reduction factors $NR^{n \epsilon [1, \ldots, N]}$ are specific to each adaptive filter channel and are assigned to each channel in advance. The adaptive filter 70 is one of the known adaptive filters, which is used in the same way for each of the filter channels, except of assuming different noise reduction factors for each channel. The adaptive filtering technique takes into consideration the noise caused by the patient's anatomy and dose and also the approximated noise of hybrid readings. The suppression of noise is made to those data points that had an excessive noise by applying a preferably floating threshold.

After the data is filtered, a convolver 78 performs a one-dimensional convolution with a ramp kernel in each of the channels 1 through N. The convolution is performed along a parallel set of readings for each of the detector rows. The data is convolved angle by angle to complete a 2D data set, covering the angular range of $\theta \in [0, \pi)$.

With continuing reference to FIGS. 1 and 2, a backprojecting means 80 performs a weighted backprojection of the convolved data into a 3D image representation. More specifically, a weighted averaging means 82 averages the plurality of readings that contribute to the hybrid reading for each channel $n \in [1, 2, \ldots, N]$, e.g. readings which contribute to each voxel v at an angle $\theta \in [0, \pi)$. A noise reduction factor determining means 84 determines a noise reduction factor that results from the weighted averaging. The weighted averaging may be different from a typical averaging because of the different cardiac weight given for the different readings that contribute to the same hybrid reading. The cardiac weights given to each reading are calculated by one of known techniques and are typically dependent on a position within a gating window within each interval of the patient's electrocardiogram and a corresponding window width. The noise reduction factors determined for each reading are stored in a reduction factors memory 86.

A weighting means 90 weights the contribution from each convolved data channel in accordance with the determined noise reduction factors. A retrieving means 92 retrieves the degree of redundancy, i.e., the noise reduction factor, associated with the readings of different projections which contribute to the voxel v at the angle $\theta$. Based on the degree of redundancy, a weighting selection means 94 determines what weight $W^n_{v,p}$ to give to each channel for a particular voxel or sub-block of voxels, $$W^n_{v,p} = W^{NAF}_{v,p} \cdot W^n(NR_{v,\theta}), \text{ where}$$

$W^n_{v,p}$ is a weight given to the reading of the projection p backprojected into the voxel v through the channel n, $W^{NAF}_{v,p}$ is a voxel position dependent combined illumination and cardiac weight applied to the reading of projection p and calculated by one of the methods known in the art, and $W^n(NR_{v,\theta})$ is a voxel dependent weighting function, where $NR_{v,\theta}$ is the noise reduction factor calculated in advance.

A combining means 96 sums the weighted contributions from each channel. A backprojector 98 backprojects the weighted sum into the image memory 52. For each ray, the weighting selection means 94 can select a single one of the channels that has the closest assigned noise reduction or can combine a fraction of the values from several or even all channels, with the closest noise reduction being weighted most heavily.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having described the preferred embodiments, the invention is now claimed to be:

1. A diagnostic imaging system, comprising:
    a means for re-binning projection data into a parallel ray format;
    a means for filtering the parallel ray format data with each of a plurality of different filter channels;
    a means for convolving the data filtered with each of the filter channels;
    a means for weighted averaging readings which contribute to each voxel v at an angle $\theta \in [0, \pi)$;
    a means for determining actual noise reduction factors to be produced by the weighted averaging; and
    a means for weighting the convolved data for each of the filter channels based on the channels' noise reduction factors, and the determined actual noise reduction factors.

2. The system as set forth in claim 1, wherein the filtering means applies different initial noise reduction factor in each of the plurality of independent filter channels, which initial noise reduction factors are predetermined and preassigned to each filter channel.

3. The system as set forth in claim 1, further including:
    a means for calculating photon noise for each data value to select an adaptive filter function for the filter channels.

4. The system as set forth in claim 1, further including:
    a means for determining what weight to give to the differently filtered convolved data values based on the determined actual noise reduction factors.

5. The system as set forth in claim 4, further including:
    a means for retrieving the determined actual noise reduction factor of readings of different projections contributing to the voxel v at angle $\theta$.

6. The system as set forth in claim 5, further including:
    a means for combining the differently filtered convolved data values prior to backprojection.

7. The system as set forth in claim 1, further including:
    a means for collecting two-dimensional projection data, each data value of the collected data being related to line integrals of an object being reconstructed taken along each ray.

8. The system as set forth in claim 1, further including:
    a means for three-dimensionally backprojecting the weighted convolved data.

9. The system as set forth in claim 1, further including:
    a means for sorting the projection data into data sets collected during each of selected cardiac phases.

10. The system as set forth in claim 1, further including:
    a CT scanner which acquires projection data within at least a plurality of selected time windows, the scanner including:
        a rotating gantry,
        a source of a cone beam radiation which traverses an examination region, and
        a radiation detector which detects the radiation after it passes through the examination region and converts it into the projection data format, which radiation source and radiation detector are oppositely positioned at the rotating gantry for continuous rotation about the examination region;
    a backprojector which reconstructs x-ray radiation received by the two-dimensional radiation detector into a volumetric image representation; and
    a display for displaying the volumetric image representation.

11. The system as set forth in claim 1, wherein the filtering is performed in independent parallel processing channels.

12. A method for connecting streak artifacts in a cone beam CT imaging system, comprising:
  re-binning projection data into a parallel ray format;
  filtering the parallel ray format data with each of a plurality of different filter channels;
  convolving the data filtered with each of the filter channels;
  weighted averaging readings which contribute to each voxel v at an angle $\theta \epsilon [0, \pi)$;
  determining actual noise reduction factors to be produced by weighted averaging; and
  weighting the convolved data for each of the filter channels based on the channels' noise reduction factors, and the determined actual noise reduction factors.

13. The method as set forth in claim 12, further including:
  applying different initial noise reduction correction factor in each independent filter channel, which initial noise reduction correction factor is predetermined and preassigned to each filter channel.

14. The method as set forth in claim 12, further including:
  calculating photon noise of the data points for selecting an adaptive filter function for the filter channels.

15. The method as set forth in claim 12, further including:
  determining what weight to give to the convolved data of each independent filter channel.

16. The method as set forth in claim 15, wherein the weighting is a number between 0 and 1.

17. The method as set forth in claim 15, further including:
  retrieving the determined actual noise reduction factors, and
  determining the convolved data weight for the voxel v at the angle $\theta$ based on the actual noise reduction factor.

18. The method as set forth in claim 15, further including:
  selecting projections of which filter channels are used to reconstruct a final image.

19. The method as set forth in claim 12, further including:
  collecting two-dimensional data, each data value of the collected data being related to line integrals of an object being reconstructed taken along each ray.

20. The method as set forth in claim 12, further including:
  three-dimensionally backprojecting the weighted convolution.

21. An image processor programmed to perform the steps of claim 12.

22. A diagnostic imaging system including:
  a source of a cone beam radiation which traverses an examination region;
  a radiation detector which detects the radiation after it passes through the examination region and converts it into an electronic projection data format;
  an image processor which reconstructs the cone beam projection data into a three-dimensional reconstructed image which image processor is programmed to perform steps of:
    re-binning the collected data into a parallel ray format;
    filtering the parallel ray format data with each of a plurality of different filter channels;
    convolving the data filtered with each of the filter channels,
    weight averaging readings contributing to each voxel v at an angle $\theta \epsilon [0, \pi)$;
    determining noise reduction factor of each contributing reading produced by the weighted averaging;
    weighting the convolved data for each of the filter channels based on, cardiac weights given to each contributing reading, and the noise reduction factor; and
  a display which displays the backprojected data in a human-viewable image format.

* * * * *